(12) United States Patent
Green (10) Patent No.: US 10,408,801 B2
(45) Date of Patent: Sep. 10, 2019

(54) DYNAMIC POST COLUMN ADDITION

(71) Applicant: Micromass UK Limited, Wilmslow (GB)

(72) Inventor: Martin Raymond Green, Bowdon (GB)

(73) Assignee: MICROMASS UK LIMITED, Wilmslow (GB)

( * ) Notice: Subject to any disclaimer, the term of this patent is extended or adjusted under 35 U.S.C. 154(b) by 41 days.

(21) Appl. No.: 15/524,835

(22) PCT Filed: Nov. 5, 2015

(86) PCT No.: PCT/GB2015/053352
§ 371 (c)(1),
(2) Date: May 5, 2017

(87) PCT Pub. No.: WO2016/071695
PCT Pub. Date: May 12, 2016

(65) Prior Publication Data
US 2017/0315101 A1    Nov. 2, 2017

(30) Foreign Application Priority Data

Nov. 5, 2014   (EP) ...................................... 14191964
Nov. 5, 2014   (GB) ................................... 1419727.1

(51) Int. Cl.
*H01J 49/00*         (2006.01)
*G01N 30/06*        (2006.01)
(Continued)

(52) U.S. Cl.
CPC ........... *G01N 30/06* (2013.01); *G01N 30/724* (2013.01); *G01N 30/7206* (2013.01); *G01N 2030/067* (2013.01); *G01N 2030/8809* (2013.01)

(58) Field of Classification Search
CPC ........ H01J 49/00; H01J 49/02; H01J 49/0431; H01J 49/0436; H01J 49/044;
(Continued)

(56) References Cited

U.S. PATENT DOCUMENTS 5,101,054 A  * 3/1992 Yamashita .......... C07F 15/0093
                                                        556/137
8,648,297 B2    2/2014 Chen et al.
(Continued)

OTHER PUBLICATIONS

Raina et al., Liquid Chromatography with Post-Column Reagent Addition of Ammonia in Methanol Coupled to Negative Ion Electrospray Ionization Tandem Mass Spectrometry for Determination of Phenoxyacid Herbicides and their Degredation Products in Surface Water, 2010, Analytical Chemistry Insights, 5, pp. 1-14.*
(Continued)

*Primary Examiner* — Jason L McCormack (57) ABSTRACT

A method of ionizing a sample is disclosed comprising performing an initial experiment comprising: (i) adding one or more reagents to an analyte sample; (ii) varying the composition and/or concentration of the one or more reagents; (iii) ionizing the analyte sample including the one or more reagents; (iv) determining the composition and/or concentration of the one or more reagents which results in a desired, improved or optimized ionization or other condition or parameter for one or more analytes of interest; and (v) determining one or more first retention times or one or more first retention time windows for the one or more analytes of interest. The method then further comprises separating an analyte sample using a first separation device and during the course of a single experimental run or acquisition varying the composition and/or concentration of one or more reagents which are added to an eluent which emerges from the first separation device. The composition and/or concentration of the one or more reagents which are added to the
(Continued)

eluent is varied at the one or more the first retention times or during the one or more the first retention time windows so that an ionization or other condition or parameter for the one or more analytes of interest is as desired or is improved or optimized.

18 Claims, 1 Drawing Sheet

(51) Int. Cl.
G01N 30/72 (2006.01)
G01N 30/88 (2006.01)

(58) Field of Classification Search
CPC .... H01J 49/0445; H01J 49/045; G01N 30/00; G01N 30/02; G01N 30/04; G01N 30/06; G01N 30/065
USPC .......................... 250/281, 282, 288
See application file for complete search history.

(56) References Cited

U.S. PATENT DOCUMENTS

| 9,400,267 | B2 | 7/2016 | Chen et al. | |
|---|---|---|---|---|
| 2008/0090298 | A1 | 4/2008 | Apffel | |
| 2011/0036973 | A1* | 2/2011 | Alonso | G01N 27/624 250/282 |
| 2014/0353493 | A1* | 12/2014 | Mordehai | H01J 49/062 250/287 |

OTHER PUBLICATIONS

Raina et al., Liquid Chromatography with Post-Column Reagent Addition of Ammonia in Methanol Coupled to Negative Ion Electrospray Ionization Tandem Mass Spectrometry . . . , 2010, Analytical Chemistry Insights, 5, pp. 1 -14. (Year: 2010).*

Raina et al., Liquid Chromatography with Post-Column Reagent Addition of Ammonia in Methanol Coupled to Negative Ion Electrospray Ionization Tandem Mass Spectrometry for Determination of Phenoxyacid Herbicides . . . , 2010, Analytical Chemistry Insights, 5, pp. 1-14. (Year: 2010).*

Raina, R. et al., "*Liquid Chromatography with Post-Column Regent Addition of Ammonia in Methanol Coupled to Negative Ion Electrospray Ionization Tandem Mass Spectrometry for Determination of Phenoxyacid Herbicides and Their Degradation Products in Surface Water*", Analytical Chemistry Insights, vol. 5, pp. 1-14, 2010.

Zhang, Y. et al., "Coupling of Liquid Chromatography with Mass Spectrometry by Desorption Electrospray Ionization", *Chemical Communications*, vol. 47, No. 14, pp. 4171, Jan. 2011.

Search and Examination Report for Application No. GB1519559.7 dated May 23, 2016.

Raina, R., et al., "Analytical Chemistry Insights Liquid chromatography with post-column Reagent Addition of Ammonia in Methanol coupled to negative Ion electrospray Ionization Tandem Mass spectrometry for Determination of phenoxyacid Herbicides and their Degradation products in surface Water," Analytical Chemistry Insights, vol. 5, pp. 1-14, 2010.

* cited by examiner

DYNAMIC POST COLUMN ADDITION

CROSS-REFERENCE TO RELATED APPLICATIONS

This application represents the U.S. National Phase of International Application number PCT/GB2015/053352 entitled "Dynamic Post Column Addition" filed 5 Nov. 2015, which claims priority from and the benefit of United Kingdom patent application No. 1419727.1 filed on 5 Nov. 2014 and European patent application No. 14191964.7 filed on 5 Nov. 2014. The entire contents of these applications are incorporated herein by reference.

BACKGROUND TO THE PRESENT INVENTION

The present invention relates to a method of ionising a sample, a method of mass spectrometry, apparatus for ionising a sample and a mass spectrometer.

In targeted analysis using mass spectrometry it is known to run one or more survey or calibration experiments using standard solutions of target analytes with or without a matrix. These survey experiments allow the optimum instrument parameters to be determined for each analyte and also allow the instrument parameters to be associated with the retention time window of each target. The conditions depend on both the target compound and the chromatographic conditions e.g. flow rate, eluent composition and temperature.

It is known to add a reagent to the eluent emerging from a liquid chromatography separator before the eluent passes to an ionisation source and is then ionised and the resulting ions are subsequently mass analysed by a mass analyser. The process of adding a reagent to the eluent emerging from a liquid chromatography separator is commonly referred to as post column addition.

The addition of a reagent downstream of a chromatographic separation (e.g. post column) and upstream of an ionisation source allows the nature of the ions which are subsequently formed by the ionisation source to be altered to optimise the conditions for analysis and detection without compromising the conditions required for separation of analyte molecules as the analyte molecules pass through the upstream chromatographic separation device.

It is known that the addition of a post column reagent may result in modification of endogenous matrix or background ions and/or specific target analytes.

N. Volpi and R. J. Linhardt "High-performance liquid chromatography-mass spectrometry for mapping and sequencing glycosaminoglycan-derived oligosaccharides" Nat Protoc. 2010 June; 5(6), p. 993-1004 discloses post-column addition of tributylamine/acetonitrile which has the advantage of causing the disappearance of certain cation adduct peaks e.g. $Na^+$, $K^+$ or $NH_4^+$ which results in mass spectra exhibiting reduced chemical noise thereby producing simplified and more readily interpretable mass spectra.

US 2008/0090298 (Apffel) discloses a method of protein analysis mass spectrometry. In one arrangement, a reagent is added to eluent from a liquid chromatography separation device to cleave crosslinking.

Yun Zhang et al: "Coupling of liquid chromatography with mass spectrometry by desorption electrospray ionisation" Chemical Communications; 1 Jan. 2011; vol. 47 no. 14; p. 4171 and US 2013/023005 (Chen) both disclose a method of desorption electrospray ionisation (DESI) wherein a solvent is added to a chromatographic effluent prior to ionisation in order to enhance ionisation efficiency.

It is desired to provide an improved mass spectrometer.

SUMMARY OF THE PRESENT INVENTION

According to an aspect there is provided a method of ionising a sample comprising:

performing an initial experiment comprising: (i) adding one or more reagents to an analyte sample; (ii) varying the composition and/or concentration of the one or more reagents; (iii) ionising the analyte sample including the one or more reagents; (iv) determining the composition and/or concentration of the one or more reagents which results in a desired, improved or optimised ionisation or other condition or parameter for one or more analytes of interest; and (v) determining one or more first retention times or one or more first retention time windows for the one or more analytes of interest; and then separating an analyte sample using a first separation device and during the course of a single experimental run or acquisition varying the composition and/or concentration of one or more reagents which are added to an eluent which emerges from the first separation device, wherein the composition and/or concentration of the one or more reagents which are added to the eluent is varied at the one or more the first retention times or during the one or more the first retention time windows so that an ionisation or other condition or parameter for the one or more analytes of interest is as desired or is improved or optimised.

US 2008/0090298 (Apffel) does not disclose varying the composition and/or concentration of reagents which are added to an eluent at one or more retention times so that ionisation for one or more analytes of interest is improved. Instead, the approach of US 2008/0090298 (Apffel) is to add a cleaving reagent to an eluent that acts on all analytes of interest eluting. The composition/concentration of the cleaving reagent which is added is not varied based on any rentention times of individual analytes. Furthermore, US 2008/0090298 (Apffel) does not disclose adding a reagent to improve ionisation of analytes of interest, nor determining the composition and/or concentration of one of more reagents which result in improved ionisation when added to analytes of interest.

Yun Zhang et al: "Coupling of liquid chromatography with mass spectrometry by desorption electrospray ionisation" Chemical Communications; 1 Jan. 2011; vol. 47 no. 14; p. 4171 does not disclose varying the composition and/or concentration of reagents which are added to an eluent at one or more retention times or during one or more retention time windows.

Similarly, US 2013/023005 (Chen) also does not disclose varying the composition and/or concentration of reagents which are added to an eluent at one or more retention times or during one or more retention time windows.

In contrast, these arrangements disclose adding solvent to an eluent without varying its concentration/composition for all analytes that elute.

There are several advantages to adding reagents during pre-scheduled time periods prior to ionization and dynamically varying the composition and/or concentration of the one or more reagents which are added to the eluent during the course of a single experimental run or acquisition in accordance with various embodiments.

According to various embodiments ionisation efficiency for particular analytes under specific ion source conditions may be optimized. For example, steroids have been found to have an improved ionization efficiency and reproducibility or response in positive ion Electrospray using ammonia $[NH_4]^+$ as a charge carrier rather than a proton $[H]^+$ or sodium $[Na]^+$ as a charge carrier.

If a compound such as a steroid is likely to elute from a liquid chromatography column at a certain time then according to an embodiment ammonium hydroxide solution may be added post column at the time the steroid is predicted to elute.

At a different time during a chromatographic run a different class of compound may elute which may have a higher ionization efficiency with a proton as the charge carrier. Accordingly, at this time the flow of ammonium hydroxide may be stopped and a flow of an acidic solution such as formic acid may be initiated according to an embodiment.

Ionisation efficiency in negative ionization mode may require different solution chemistry than for positive ion mode. At a particular retention time an eluting target compound may have a better ionization efficiency in negative ion mode with post column addition of a suitable reagent solution. At a different retention time an eluting target may be preferentially analysed in positive ion mode. Accordingly, the mass spectrometer may be programmed to switch from positive to negative ion mode at a pre-determined time according to an embodiment and at the same time the nature of the reagent added post column may be changed to suit or optimise the ionization conditions.

Another example of the utility of the present embodiments is ion stability. A labile compound may be more stable with a sodium ion as a charge carrier rather than with a proton and hence the compound will be less likely to fragment during ionization or subsequent analysis. At the time the compound elutes a solution of sodium chloride may be added post column according to an embodiment in order to promote formation of the sodiated analyte ion. Once the labile compound has eluted from the column the nature of the additive may then be changed in order to optimise conditions for subsequently eluting targets.

The method may further comprise ionising the eluent and/or ionising the eluent including the one or more reagents.

The step of ionising the eluent and/or ionising the eluent including the one or more reagents may result in the generation of first ions.

The method may further comprise mass analysing the first ions.

The method may further comprise separating the first ions according to their ion mobility, collision cross section, interaction cross section or differential ion mobility.

The first separation device may comprise a liquid chromatography separation device. Alternatively, the first separation device may comprise a gas chromatography separation device.

The step of adding the one or more reagents to the eluent may modify, vary, increase or decrease the generation of one or more matrix or background ions.

The step of adding the one or more reagents to the eluent may modify, vary, increase or decrease the generation of one or more analyte ions.

The step of adding the one or more reagents to the eluent may modify, vary, increase or decrease the ionisation efficiency of one or more matrix or background ions.

The step of adding the one or more reagents to the eluent may modify, vary, increase or decrease the ionisation efficiency of one or more analyte ions.

The step of adding the one or more reagents to the eluent may modify, vary, increase or decrease the stability of one or more matrix or background ions.

The step of adding the one or more reagents to the eluent may modify, vary, increase or decrease the stability of one or more analyte ions.

The step of adding the one or more reagents to the eluent may modify, vary, increase or decrease one or more physico-chemical properties of one or more matrix or background ions.

The step of adding the one or more reagents to the eluent may modify, vary, increase or decrease one or more physico-chemical properties of one or more analyte ions.

According to another aspect there is provided a method of mass spectrometry, comprising a method as described above.

According to an aspect there is provided an apparatus for ionising a sample comprising:

a first separation device which in use separates an analyte sample;

wherein, in use, an initial experiment is performed comprising: (a) adding one or more reagents to an analyte sample; (b) varying the composition and/or concentration of the one or more reagents; (c) ionising the analyte sample including the one or more reagents; (d) determining the composition and/or concentration of the one or more reagents which results in a desired, improved or optimised ionisation or other condition or parameter for one or more analytes of interest; and (e) determining one or more first retention times or one or more first retention time windows for the one or more analytes of interest;

the apparatus further comprising a control system arranged and adapted:

(i) to separate an analyte sample using the first separation device and during the course of a single experimental run or acquisition to vary the composition and/or concentration of one or more reagents which are added to an eluent which emerges from the first separation device, wherein the composition and/or concentration of the one or more reagents which are added to the eluent is varied at the one or more the first retention times or during the one or more the first retention time windows so that an ionisation or other condition or parameter for the one or more analytes of interest is as desired or is improved or optimised.

According to another aspect there is provided a mass spectrometer comprising apparatus as described above.

According to another aspect there is provided a method of ionising a sample comprising:

adding one or more reagents to an eluent which emerges from a first separation device to form a first sample; and ionising the first sample;

wherein the method further comprises:

varying the composition and/or concentration of the one or more reagents which are added to the eluent during the course of a single experimental run or acquisition.

The method may further comprise separating one or more analytes using the first separation device.

The first separation device may comprise a liquid chromatography separation device.

The first separation device may alternatively comprise a gas chromatography separation device.

The step of adding one or more reagents to the eluent may modify, vary, increase or decrease the generation of one or more matrix or background ions.

The step of adding one or more reagents to the eluent may modify, vary, increase or decrease the generation of one or more analyte ions.

The step of adding one or more reagents to the eluent may modify, vary, increase or decrease the ionisation efficiency of one or more matrix or background ions.

The step of adding one or more reagents to the eluent may modify, vary, increase or decrease the ionisation efficiency of one or more analyte ions.

The step of adding one or more reagents to the eluent may modify, vary, increase or decrease the stability of one or more matrix or background ions.

The step of adding one or more reagents to the eluent may modify, vary, increase or decrease the stability of one or more analyte ions.

The step of adding one or more reagents to the eluent may modify, vary, increase or decrease one or more physico-chemical properties of one or more matrix or background ions.

The step of adding one or more reagents to the eluent may modify, vary, increase or decrease one or more physico-chemical properties of one or more analyte ions.

The step of ionising the first sample may result in the generation of first ions.

The method may further comprise mass analysing the first ions.

The method may further comprise separating the first ions according to their ion mobility, collision cross section or differential ion mobility.

According to another aspect there is provided a method of mass spectrometry as described above.

According to another aspect there is provided apparatus for ionising a sample comprising:

a first separation device;

a second device arranged and adapted to add one or more reagents to an eluent which emerges, in use, from the first separation device to form a first sample;

an ion source arranged and adapted to ionise the first sample; and a control system arranged and adapted to vary the composition and/or concentration of the one or more reagents which are added to the eluent during the course of a single experimental run or acquisition.

According to another aspect there is provided a mass spectrometer comprising apparatus as described above.

According to another aspect there is provided a method of ionising a sample comprising:

dynamically varying the composition and/or concentration of one or more reagents which are added to an eluent which emerges, in use, from a first separation device prior to ionising the eluent, wherein the composition and/or concentration of the one or more reagents are dynamically varied during the course of a single experimental run or acquisition.

According to another aspect there is provided apparatus for ionising a sample comprising:

a first separation device; and a second device arranged and adapted to dynamically vary the composition and/or concentration of one or more reagents which are added to eluent emerging from the first separation device prior to ionising the eluent, wherein the composition and/or concentration of the one or more reagents are dynamically varied by the second device during the course of a single experimental run or acquisition.

According to another aspect there is provided a method of ionisation comprising:

producing analyte droplets or analyte vapour;

causing second droplets or vapour and ions to interact with the analyte droplets or analyte vapour in order to produce analyte ions; and dynamically varying the composition and/or concentration of the second droplets or vapour and/or ions during the course of a single experimental run or acquisition.

The method may further comprise chromatographically separating an analyte solution or analyte vapour prior to producing the analyte droplets or analyte vapour.

The method may further comprise using a nebuliser to produce the analyte droplets or analyte vapour.

The method may further comprise using an Electrospray emitter or nebuliser to produce the second droplets or vapour and/or ions.

The method may further comprise using an ultrasonic source to produce the analyte droplets or analyte vapour.

According to another aspect there is provided a method of Extractive Electrospray comprising a method as described above.

According to another aspect there is provided a method of ionisation comprising:

adding one or more reagents to an analyte solution to form a first sample;

passing the first sample through an Electrospray emitter;

directing analyte droplets or vapour and/or ions emitted from the Electrospray emitter against a surface in order to produce analyte ions from analytes desorbed by the surface; and dynamically varying the composition and/or concentration of the one or more reagents during the course of a single experimental run or acquisition.

According to another aspect there is provided a method of Desorption Electrospray Ionisation ("DESI") comprising a method as described above.

According to another aspect there is provided a method of mass spectrometry comprising a method as described above.

According to another aspect there is provided apparatus for ionising a sample comprising:

a device arranged and adapted to produce analyte droplets or analyte vapour and to cause second droplets or vapour and ions to interact with the analyte droplets or analyte vapour in order to produce analyte ions; and a control system arranged and adapted to dynamically vary the composition and/or concentration of the second droplets or vapour and/or ions during the course of a single experimental run or acquisition.

The apparatus may further comprise a chromatographic separation device for chromatographically separating an analyte solution or analyte vapour prior to the device producing the analyte droplets or analyte vapour.

The apparatus may further comprise a nebuliser arranged and adapted to produce the analyte droplets or analyte vapour.

The apparatus may further comprise an Electrospray emitter or nebuliser arranged and adapted to produce the second droplets or vapour and/or ions.

The apparatus may further comprise an ultrasonic source arranged and adapted to produce the analyte droplets or analyte vapour.

According to another aspect there is provided an Extractive Electrospray ion source comprising apparatus as described above.

According to another aspect there is provided apparatus for ionising a sample comprising:

a device arranged and adapted to add one or more reagents to an analyte solution to form a first sample;

a device arranged and adapted to pass the first sample through an Electrospray emitter;

a device arranged and adapted to direct analyte droplets or vapour and/or ions emitted from the Electrospray emitter against a surface in order to produce analyte ions from analytes desorbed by the surface; and a control system arranged and adapted to dynamically vary the composition and/or concentration of the one or more reagents during the course of a single experimental run or acquisition.

According to another aspect there is provided a Desorption Electrospray Ionisation ("DESI") ion source comprising apparatus as described above.

According to another aspect there is provided a mass spectrometer comprising apparatus as described above.

According to another aspect there is provided a method of ionising a sample comprising:

separating an analyte sample using a first separation device and performing an initial or survey scan;

determining from the initial or survey scan a predicted retention time or a predicted retention time window for one or more analytes; and then separating the analyte sample using the first separation device and selectively varying the composition and/or concentration of one or more reagents which are added to an eluent which emerges from the first separation device, wherein the composition and/or concentration of the one or more reagents is selectively varied in order to modify, vary, increase or decrease an ionisation or other condition or parameter.

According to another aspect there is provided a method of ionising a sample comprising:

performing one or more initial experiments to determine: (i) the composition and/or concentration of one or more reagents which when added to one or more analytes of interest results in a desired, improved or optimised ionisation or other condition or parameter for the one or more analytes of interest; and (ii) one or more first retention times or one or more first retention time windows for the one or more analytes of interest; and then separating an analyte sample using a first separation device and during the course of a single experimental run or acquisition varying the composition and/or concentration of one or more reagents which are added to an eluent which emerges from the first separation device at the one or more the first retention times or during the one or more the first retention time windows so that an ionisation or other condition or parameter for the one or more analytes of interest is as desired or is improved or optimised.

According to another aspect there is provided a method of ionising a sample comprising:

performing an initial experiment comprising: (i) adding one or more reagents to an analyte sample; (ii) varying the composition and/or concentration of the one or more reagents; (iii) ionising the analyte sample including the one or more reagents; and (iv) determining the composition and/or concentration of the one or more reagents which results in a desired, improved or optimised ionisation or other condition or parameter for one or more analytes of interest; and then separating an analyte sample using a first separation device and performing an initial or survey scan to determine one or more first retention times or one or more first retention time windows for the one or more analytes of interest; and then separating the analyte sample using the first separation device and during the course of a single experimental run or acquisition varying the composition and/or concentration of one or more reagents which are added to an eluent which emerges from the first separation device, wherein the composition and/or concentration of the one or more reagents which are added to the eluent is varied at the one or more the first retention times or during the one or more the first retention time windows so that an ionisation or other condition or parameter for the one or more analytes of interest is as desired or is improved or optimised.

According to another aspect there is provided apparatus for ionising a sample comprising:

a first separation device which in use separates an analyte sample; and a control system arranged and adapted:

(i) to perform an initial or survey scan;

(ii) to determine from the initial or survey scan a predicted retention time or a predicted retention time window for one or more analytes; and then (iii) to cause the analyte sample to separate using the first separation device and to selectively vary the composition and/or concentration of one or more reagents which are added to an eluent which emerges from the first separation device, wherein the composition and/or concentration of the one or more reagents is selectively varied in order to modify, vary, increase or decrease an ionisation or other condition or parameter.

According to an aspect there is provided an apparatus for ionising a sample comprising:

a first separation device which in use separates an analyte sample;

wherein, in use, one or more initial experiments are performed to determine: (a) the composition and/or concentration of one or more reagents which when added to one or more analytes of interest results in a desired, improved or optimised ionisation or other condition or parameter for the one or more analytes of interest; and (b) one or more first retention times or one or more first retention time windows for the one or more analytes of interest;

the apparatus further comprising a control system arranged and adapted:

(i) to separate an analyte sample using the first separation device and during the course of a single experimental run or acquisition to vary the composition and/or concentration of one or more reagents which are added to an eluent which emerges from the first separation device at the one or more the first retention times or during the one or more the first retention time windows so that an ionisation or other condition or parameter for the one or more analytes of interest is as desired or is improved or optimised.

According to an aspect there is provided an apparatus for ionising a sample comprising:

a first separation device which in use separates an analyte sample;

wherein, in use, an initial experiment is performed comprising: (a) adding one or more reagents to an analyte sample; (b) varying the composition and/or concentration of the one or more reagents; (c) ionising the analyte sample including the one or more reagents; and (d) determining the composition and/or concentration of the one or more reagents which results in a desired, improved or optimised ionisation or other condition or parameter for one or more analytes of interest;

the apparatus further comprising a control system arranged and adapted:

(i) to separate an analyte sample using the first separation device and to perform an initial or survey scan to determine one or more first retention times or one or more first retention time windows for the one or more analytes of interest; and then (ii) to separate the analyte sample using the first separation device and during the course of a single experimental run or acquisition to vary the composition and/or concentration of one or more reagents which are added to an eluent which emerges from the first separation device, wherein the composition and/or concentration of the one or more reagents which are added to the eluent is varied at the one or more the first retention times or during the one or more the first retention time windows so that an ionisation or other condition or parameter for the one or more analytes of interest is as desired or is improved or optimised.

According to an aspect there is provided a method of mass spectrometry comprising:

separating analyte molecules in a first separation device;

providing a second device controlling introduction of reagent downstream of the separation device wherein the reagent changes the physicochemical nature of an analyte eluting from the first separation device or the physicochemical nature of ions subsequently formed in an ionization source;

providing an ionization source downstream of the first separation device and second reagent introduction device;

further analyzing ions formed in the ionization source using a downstream mass analyser and or mobility analyser;

wherein:

the optimum type and concentration of reagent is determined for each analyte in a first survey experiment or first survey experiments; and a control system is preferably provided to vary the type and/or concentration of the reagent dynamically as a function of the elution time of analytes from the first separation device such that the optimum type and/or concentration of reagent is present in the eluent stream as each analyte elutes.

The optimum type and concentration may be such that the analyte ions formed in the ion source are optimized for: (i) type and/or efficiency of product ion formation by Collision Induced Dissociation ("CID"), Electron Transfer Dissociation ("ETD"), Electron Capture Dissociation ("ECD") or Surface Induced Dissociation ("SID"); (ii) ion mobility separation of co-eluting compounds; (iii) ionisation efficiency including positive or negative ion operation or switching experiments; and (iv) mass to charge ratio value to avoid mass to charge ratio interferences.

The reagent may control or alter the type or number of charge carriers on the analyte ion.

The reagent may reduce, oxidize or otherwise react with the analyte in solution.

The reagent may comprise a derivatisation reagent.

The various disclosed embodiments are concerned with optimising the solution composition after chromatographic separation and prior to ionization to allow for optimum ionization of each target compound. A control system may be arranged to allow the composition of the solvent to be adjusted during the chromatographic run.

The chemistry of ion formation may be altered on a per analyte basis. This allows optimum analysis conditions for each analyte. In contrast, conventionally the ion formation chemistry is maintained constant for a given experiment and hence the performance is a compromise for all or some of the analytes delivered to the mass spectrometer.

According to various embodiments the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The mass spectrometer may further comprise a device arranged and adapted to supply an AC or RF voltage to the electrodes. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage may have a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The mass spectrometer may comprise a chromatography detector.

The chromatography detector may comprise a destructive chromatography detector preferably selected from the group consisting of: (i) a Flame Ionization Detector ("FID"); (ii) an aerosol-based detector or Nano Quantity Analyte Detector ("NQAD"); (iii) a Flame Photometric Detector ("FPD"); (iv) an Atomic-Emission Detector ("AED"); (v) a Nitrogen Phosphorus Detector ("NPD"); and (vi) an Evaporative Light Scattering Detector ("ELSD").

Additionally or alternatively, the chromatography detector may comprise a non-destructive chromatography detector preferably selected from the group consisting of: (i) a fixed or variable wavelength UV detector; (ii) a Thermal Conductivity Detector ("TCD"); (iii) a fluorescence detector; (iv) an Electron Capture Detector ("ECD"); (v) a conductivity monitor; (vi) a Photoionization Detector ("PID"); (vii) a Refractive Index Detector ("RID"); (viii) a radio flow detector; and (ix) a chiral detector.

The ion guide may be maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

According to an embodiment analyte ions may be subjected to Electron Transfer Dissociation ("ETD") fragmentation in an Electron Transfer Dissociation fragmentation device. Analyte ions are preferably caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions;

and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions preferably comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenan-threne; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

The process of Electron Transfer Dissociation fragmentation may comprise interacting analyte ions with reagent ions, wherein the reagent ions comprise dicyanobenzene, 4-nitrotoluene or azulene.

BRIEF DESCRIPTION OF THE DRAWINGS

Various embodiments will now be described, by way of example only, and with reference to the accompanying drawing in which.

DETAILED DESCRIPTION OF PREFERRED EMBODIMENT

An embodiment will now be described in more detail.

Figure 1:
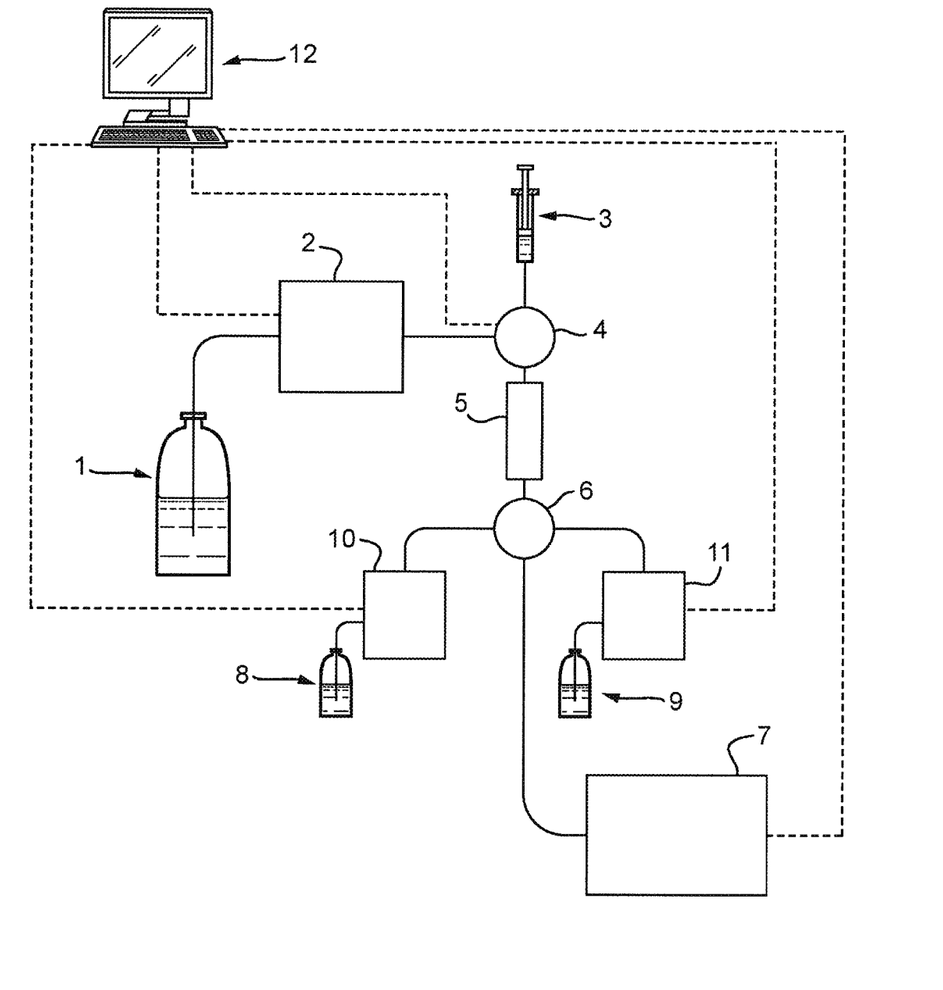
FIG. 1 shows a liquid chromatography device according to an embodiment.

FIG. 1 shows a schematic of apparatus which may be utilised according to an embodiment. A Liquid Chromatography ("LC") sample 1 is driven by a liquid chromatography pump 2 to a separating liquid chromatography column 5. Eluent which emerges from the liquid chromatography column 5 may then be passed to an ion source region of a mass spectrometer 7.

An injector device 4 is arranged to allow sample to be introduced into the solvent flow via a syringe 3. Analyte introduced via the injector 4 may be separated chromatographically before being ionized in the solvent stream.

A cross type mixing adaptor 6 may be situated between the end of the liquid chromatography column 5 and the ion source region of the mass spectrometer 7. The mixing adaptor 6 may comprise a known low dead volume fitting and may comprise essentially a passive device. However, according to an alternative embodiment an automated switching valve arrangement may be used.

One or more post column derivatisation reagent solutions 8,9 may be driven into the post column solvent flow using separate pumps 10,11. The one or more reagent solutions 8,9 may be mixed with the solvent flow and the analyte eluting from the liquid chromatography column 5 thereby allowing a high degree of control of the solution and ionization chemistry at specific times after analyte injection.

A control device 12 may be attached or connected to the liquid chromatography pump 2 and/or the reagent pumps 10,11 and/or the injector 4 and/or the mass spectrometer 7.

In operation a sample may be injected into the eluent flow under starting conditions. Simultaneously, a solvent composition gradient may be initiated using the liquid chromatography pump 2. The mass spectrometer 7 may then be arranged to begin to record mass spectral data of ions formed in the ionization region.

At one or more predetermined times after sample injection one or both pumps 10,11 may be arranged to either introduce (or not introduce) reagent 8,9 into the flow exiting the liquid chromatography column 5 in order to optimize system performance.

The flow rate of the solvent through the analytical column 5 may be arranged to be in the range of nano liters per minute to hundreds of micro liters per minute. The flow rate of the post column reagents 8,9 may be arranged to be lower than the flow rate of the liquid chromatography solvent so that no significant dilution of the analyte occurs which might otherwise reduce or vary the ionization efficiency.

The concentration of the reagent(s) 8,9 may be adjusted with respect to the flow rate of the liquid chromatography solvent and the flow rate of the reagent(s) 8,9 in order to achieve the desired concentration of the reagent(s) 8,9 in the solvent flow entering the ionization region of the mass spectrometer 7.

For example, the liquid chromatography solvent flow rate may be set at 800 μL/min and the reagent flow may be set at 8 μL/min. This gives a dilution factor of 1% for the analyte. However, the reagent concentration is diluted by 100 times. Therefore, to achieve a concentration of 1 mM of reagent in the sample flow a concentration of 100 mM reagent must be used.

There are several advantages to adding reagents during pre-scheduled time periods prior to ionization according to various embodiments.

Ionisation efficiency for particular analytes under specific ion source conditions may be optimized. For example, steroids have been found to have an improved ionization efficiency and reproducibility or response in positive ion Electrospray using ammonia $[NH_4]^+$ as a charge carrier rather than a proton $[H]^+$ or sodium $[Na]^+$ as a charge carrier.

If a compound such as a steroid is likely to elute from a liquid chromatography column at a certain time then according to an embodiment ammonium hydroxide solution may be added post column at this particular time.

At a different time in the chromatographic run a different class of compound may elute which has higher ionization efficiency with a proton as the charge carrier. At this time the flow of ammonium hydroxide may be stopped and a flow of an acidic solution such as formic acid may instead be initiated according to an embodiment.

Ionisation efficiency in negative ionization mode may require different solution chemistry than for positive ion mode. At a particular retention time an eluting target compound may have a better ionization efficiency in negative ion mode with post column addition of a suitable reagent solution. At a different retention time an eluting target may be preferentially analysed in positive ion mode. The mass spectrometer may be programmed to switch from positive to negative ion mode at a pre-determined time according to an embodiment. At the same time the nature of the reagent added post column may be changed to suit the ionization conditions.

Another example of the utility of the various embodiments is ion stability. A labile compound may be more stable with a sodium ion as a charge carrier rather than with a proton and hence the compound will be less likely to fragment during ionization or subsequent analysis. At the time the compound elutes a solution of sodium chloride may be added post column according to an embodiment in order to promote formation of the sodiated analyte ion. Once the labile compound has eluted from the column the nature of the additive may then be changed in order to optimise conditions for subsequently eluting targets.

In another embodiment the disclosed approach may be used to optimize or improve the ion mobility separation or differential ion mobility separation of isomers or the ion mobility separation of analytes from endogenous matrix or background ions. For example, changing the charge carrier may allow isomeric pairs of carbohydrates to the separated. Structurally related carbohydrate ions may need different charge carriers for optimum ion mobility separation. It is known that the charge state of peptide ions influences the ion mobility separation of isomers. As the retention time of these compounds is known a supercharging reagent such as meta nitrobenzyl alcohol ("MNBA") or sulpholane may be added post column at the appropriate time to allow efficient ion mobility separation.

Selective adduction or derivatisation may be used to change the collision cross section of a target analyte to allow ion mobility separation from endogenous background at particular retention times. Shift reagents such as crown ethers are also known. It may be determined that different target analytes at different retention times require different charge carriers or adducts, derivatives or other reactions to optimize subsequent ion mobility separation.

In another embodiment the chemical nature of the target analyte may be altered at a specific retention time to optimize or direct the fragmentation pathways for Collisional Induced Dissociation or for other fragmentation methods.

Controlling the nature of the analyte ion produced using post column addition of one or more reagents may be used to produce more intense product ions or more characteristic or unique product ions or yield more informative or complimentary product ion information during subsequent fragmentation.

For example, it has been shown that the addition of alkali metal ions to sphigomyalin in positive ion Electrospray yields characteristic Collision Induced Dissociation ("CID") product ions from both the long chain base and the fatty acid. These fragments may then be used to identify and quantify the compound.

In another embodiment post column addition of a reagent may be used to deliberately and selectively change the mass to charge ratio value of the target by adduction or derivatisation or reaction such that the mass to charge ratio of the target is resolved from a co-eluting interference or background ion.

Post column addition of reagent may be performed for Liquid Chromatography ("LC") or Gas Chromatography ("GC").

The above examples are compound specific. For example, analyzing a first target with a potassium ion as charge carrier may result in the optimum ion mobility separation or generation of a unique product ion for Multiple Reaction Monitoring ("MRM"). In this case during the elution of this target KCl solution may be added post column to the Liquid Chromatography ("LC") flow. At a second time in the chromatographic separation a second target may elute. If the second target forms a protonated cation then this may provide the best separation or fragmentation characteristics. In this case, the flow of KCl may be stopped and if required a flow of a second reagent may be initiated to ensure that the conditions post column result in formation of a protonated ion.

According to an embodiment the nature, concentration or presence of one or more post column reagents may be dynamically varied in order to optimize the conditions for subsequent analysis of each target compound eluting from the chromatograph.

The conditions required for each target ion may be determined using standards to develop a method in which the control of post column reagent addition is synchronized to the start of the chromatographic separation.

An initial survey scan or survey experiment may be performed prior to the main experimental run using the same sample 1. The initial survey scan or experiment may include determining the retention times and/or retention time windows of analytes of interest based on the time at which they elute from the liquid chromatography column 5.

The initial survey scan or survey experiment may also include adjusting the composition and/or concentration of reagents added into the flow exiting the liquid chromatography column 5, in order to determine what concentration and/or composition of reagents results in improved ionisation efficiency of the individual analytes of interest eluting from the chromatography column 5.

The results of the survey scan or survey experiment may then be used to determine what composition and/or concentration of reagents should be added into the flow exiting the chromatography column 5 during the course of the main experimental run, and at what time the during the course of the main experimental run the composition and/or concentration of reagents being added should be varied, so that the ionisation of the individual analytes of interest is improved as they elute from the chromatography column. For example, the results of the initial survey scan or survey experiment may be used to determine at what times reagents 8,9 should be introduced (or not introduced) into the flow exiting the chromatography column 5 during the course of the main experimental run.

Suppose, for example, that it is determined during a survey scan or survey experiment that a first analyte of interest has a retention time $t_1$, and that the ionisation efficiency of said analyte of interest is improved when mixed with a particular reagent 8 (at a particular concentration). Based on this, reagent 8 may then be introduced into the flow exiting the liquid chromatography column 5 at time $t_1$ during the main experimental run, so that the ionisation efficiency of said analyte of interest emerging at that time is optimised. The composition and/or concentration of reagents being added to the flow may similarly be varied at other times during the main experimental run, so as to improve the ionisation efficiency of other analytes of interest emerging from the chromatography column at those other times (based on the results of the initial survey scan or survey experiment).

Various alternative embodiments are contemplated.

According to an alternative embodiment the reagent may comprise a deuterated compound in order to perform hydrogen deuterium exchange ("HDX") reactions of selected target ions.

Reagent may be added in the vapour phase to effect the same optimization for individual target ions as described for the solution phase. For example, in extractive Electrospray droplets or vapour containing neutral analytes are produced using a first nebulising apparatus. This may be after chromatographic separation. A second independent source of Electrospray droplets and ions from an Electrospray emitter or nebuliser may then be introduced into the analyte vapour to produce analyte ions by secondary Electrospray ionisation. The composition of the solution in the second Electrospray nebulizer may be dynamically altered depending on the analyte to optimize the chemistry of ion formation.

Extractive Electrospray may be used to ionise analytes in solution with no chromatographic separation. For example, in combinatorial chemistry different analyte solutions may be placed in discrete vials or wells and then nebulised in turn. Nebulisation may be performed, for example, using ultrasonic agitation. If the nature of the compound is known then the composition of the extractive Electrospray solution may be altered between the analysis of different vials in order to optimize the analysis conditions.

In Desorption Electrospray Ionisation ("DESI") ions and vapour from an Electrospray emitter are directed towards a target surface and produce ions from analytes desorbed from the surface. According to an embodiment the nature of the ions formed may be altered by adding a reagent to the solution running through the Electrospray emitter in order to optimize the performance of the system. The nature of the reagent may be changed with respect to the spatial position of the sprayer and the analyte may be separated spatially prior to ionization.

Although the present invention has been described with reference to preferred embodiments, it will be understood by those skilled in the art that various changes in form and detail may be made without departing from the scope of the invention as set forth in the accompanying claims.

The invention claimed is:

1. A method of ionising a sample comprising:
    performing an initial survey experiment comprising: (i) adding one or more reagents to an analyte sample; (ii) varying the composition and/or concentration of said one or more reagents; (iii) ionising said analyte sample including said one or more reagents; (iv) determining the composition and/or concentration of said one or more reagents which results in a desired, improved or optimised ionisation or other condition or parameter for one or more analytes of interest; and (v) determining one or more first retention times or one or more first retention time windows for said one or more analytes of interest; and
    after the initial survey experiment, performing a main experiment comprising:
        introducing an analyte sample into a first separation device, the analyte sample comprising one or more of the analytes of interest;
        separating the one or more analytes of interest using the first separation device such that the one or more analytes of interest elute from the first separation device at one or more retention times or during one or more retention time windows; and
        varying the composition and/or concentration of one or more reagents which are added to an eluent which emerges from said first separation device during the course of a single experimental run or acquisition, such that the composition and/or concentration of the one or more reagents is varied in the time period between the introduction of the analyte sample into the first separation device and the time at which the final analyte of interest to elute from the separation device finishes eluting from the separation device,
    wherein the composition and/or concentration of said one or more reagents which are added to said eluent is varied at said one or more said first retention times or during said one or more said first retention time windows so that an ionisation or other condition or parameter for said one or more analytes of interest is as desired or is improved or optimised.

2. A method as claimed in claim 1, further comprising ionising said eluent and/or ionising said eluent including said one or more reagents.

3. A method as claimed in claim 2, wherein the step of ionising said eluent and/or ionising said eluent including said one or more reagents results in the generation of first ions.

4. A method as claimed in claim 3, further comprising mass analysing said first ions.

5. A method as claimed in claim 3, further comprising separating said first ions according to their ion mobility, collision cross section, interaction cross section or differential ion mobility.

6. A method as claimed in claim 1, wherein said first separation device comprises a liquid chromatography separation device.

7. A method as claimed in claim 1, wherein said first separation device comprises a gas chromatography separation device.

8. A method as claimed in claim 1, wherein the step of adding said one or more reagents to said eluent modifies, varies, increases or decreases the generation of one or more matrix or background ions.

9. A method as claimed in claim 1, wherein the step of adding said one or more reagents to said eluent modifies, varies, increases or decreases the generation of one or more analyte ions.

10. A method as claimed in claim 1, wherein the step of adding said one or more reagents to said eluent modifies, varies, increases or decreases the ionisation efficiency of one or more matrix or background ions.

11. A method as claimed in claim 1, wherein the step of adding said one or more reagents to said eluent modifies, varies, increases or decreases the ionisation efficiency of one or more analyte ions.

12. A method as claimed in claim 1, wherein the step of adding said one or more reagents to said eluent modifies, varies, increases or decreases the stability of one or more matrix or background ions.

13. A method as claimed in claim 1, wherein the step of adding said one or more reagents to said eluent modifies, varies, increases or decreases the stability of one or more analyte ions.

14. A method as claimed in claim 1, wherein the step of adding said one or more reagents to said eluent modifies, varies, increases or decreases one or more physico-chemical properties of one or more matrix or background ions.

15. A method as claimed in claim 1, wherein the step of adding said one or more reagents to said eluent modifies, varies, increases or decreases one or more physico-chemical properties of one or more analyte ions.

16. A method of mass spectrometry, comprising:

performing an initial survey experiment comprising: (i) adding one or more reagents to an analyte sample; (ii) varying the composition and/or concentration of said one or more reagents; (iii) ionising said analyte sample including said one or more reagents; (iv) determining the composition and/or concentration of said one or more reagents which results in a desired, improved or optimised ionisation or other condition or parameter for one or more analytes of interest; and (v) determining one or more first retention times or one or more first retention time windows for said one or more analytes of interest; and after the initial survey experiment, performing a main experiment comprising:

introducing an analyte sample into a first separation device, the analyte sample comprising one or more of the analytes of interest;

separating the one or more analytes of interest using the first separation device such that the one or more analytes of interest elute from the first separation device at one or more retention times or during one or more retention time windows; and varying the composition and/or concentration of one or more reagents which are added to an eluent which emerges from said first separation device during the course of a single experimental run or acquisition, such that the composition and/or concentration of the one or more reagents is varied in the time period between the introduction of the analyte sample into the first separation device and the time at which the final analyte of interest to elute from the separation device finishes eluting from the separation device, wherein the composition and/or concentration of said one or more reagents which are added to said eluent is varied at said one or more said first retention times or during said one or more said first retention time windows so that an ionisation or other condition or parameter for said one or more analytes of interest is as desired or is improved or optimised.

17. Apparatus for ionising a sample comprising:

a first separation device which in use separates an analyte sample;

wherein, in use, an initial survey experiment is performed comprising: (a) adding one or more reagents to an analyte sample; (b) varying the composition and/or concentration of said one or more reagents; (c) ionising said analyte sample including said one or more reagents; (d) determining the composition and/or concentration of said one or more reagents which results in a desired, improved or optimised ionisation or other condition or parameter for one or more analytes of interest; and (e) determining one or more first retention times or one or more first retention time windows for said one or more analytes of interest;

said apparatus further comprising a control system arranged and adapted to perform a main experiment after the initial survey experiment has been performed, the main experiment comprising:

(i) introducing an analyte sample into the first separation device, the analyte sample comprising one or more of the analytes of interest;

(ii) separating the one or more analytes of interest using said first separation device such that the one or more analytes of interest elute from the first separation device at one or more retention times or during one or more retention time windows; and (iii) varying the composition and/or concentration of one or more reagents which are added to an eluent which emerges from said first separation device during the course of a single experimental run or acquisition, such that the composition and/or concentration of the one or more reagents is varied in the time period between the introduction of the analyte sample into the first separation device and the time at which the final analyte of interest to elute from the separation device finishes eluting from the separation device, wherein the composition and/or concentration of said one or more reagents which are added to said eluent is varied at said one or more said first retention times or during said one or more said first retention time windows so that an ionisation or other condition or parameter for said one or more analytes of interest is as desired or is improved or optimised.

18. An apparatus as claimed in claim 17, the apparatus arranged within a mass spectrometer system.

* * * * *